(12) United States Patent
Zhan et al.

(10) Patent No.: US 10,314,998 B2
(45) Date of Patent: Jun. 11, 2019

(54) BREATHING MASK

(71) Applicant: BMC Medical Co., Ltd., Beijing (CN)

(72) Inventors: Yifeng Zhan, Beijing (CN); Zhi Zhuang, Beijing (CN)

(73) Assignee: BMC MEDICAL CO., LTD, Beijing (CN)

(*) Notice: Subject to any disclaimer, the term of this patent is extended or adjusted under 35 U.S.C. 154(b) by 726 days.

(21) Appl. No.: 15/008,401

(22) Filed: Jan. 27, 2016

(65) Prior Publication Data

US 2016/0136375 A1 May 19, 2016

Related U.S. Application Data

(63) Continuation of application No. PCT/CN2014/088757, filed on Oct. 16, 2014.

(30) Foreign Application Priority Data

Sep. 1, 2014 (CN) .......................... 2014 1 0440090

(51) Int. Cl.
 *A61M 16/06* (2006.01)
 *A61M 16/08* (2006.01)
(52) U.S. Cl.
 CPC .... *A61M 16/0644* (2014.02); *A61M 16/0638* (2014.02); *A61M 16/0611* (2014.02); *A61M 16/0816* (2013.01)
(58) Field of Classification Search
 CPC .............................. A61M 16/00; A61M 16/06; A61M 16/0605; A61M 16/0611; A61M 16/0616;
(Continued)

(56) References Cited

U.S. PATENT DOCUMENTS

2005/0005940 A1 1/2005 Gunaratnam
2007/0044804 A1* 3/2007 Matula, Jr. ............ A61M 16/06
 128/206.21
(Continued)

FOREIGN PATENT DOCUMENTS

CN 103052421 A 4/2013
WO 2007021777 A2 2/2007
(Continued)

OTHER PUBLICATIONS

Second Office Action from counterpart Chinese Application CN104208789A, dated Oct. 17, 2016.
(Continued)

*Primary Examiner* — Jan Christopher L Merene
*Assistant Examiner* — Joseph D. Boecker
(74) *Attorney, Agent, or Firm* — Flener IP & Business Law, LLC; Zareefa B. Flener

(57) ABSTRACT

The present invention relates to a breathing mask for use in a respirator, comprising a receiving cover comprising an engagement portion for engaging a patient's mouth portion and/or nose portion, a connection portion connected to a breathing pipe, and an elastic deformable portion for connecting the engagement portion with the connection portion; a bracket assembly, comprising a forehead support disposed external of the connection portion and a receiving cover fixing frame fixedly disposed external of the engagement portion, and an elastic member for connecting the forehead support with the receiving cover fixing frame from a bottom of the receiving cover. The breathing mask for use in a respirator according to the present invention may achieve automatic adjustment of the forehead support without manual assistant adjustment.

19 Claims, 3 Drawing Sheets

(58) Field of Classification Search
 CPC .......... A61M 16/0622; A61M 16/0633; A61M 16/0638; A61M 16/0644; A61M 16/065; A61M 16/0655; A61M 16/0683; A62B 18/02
 See application file for complete search history.

(56) References Cited

U.S. PATENT DOCUMENTS

| | | | | |
|---|---|---|---|---|
| 2009/0223521 A1* | 9/2009 | Howard | ................ | A61M 16/06 128/206.23 |
| 2009/0223523 A1* | 9/2009 | Chang | ................... | A62B 18/08 128/207.11 |
| 2011/0048425 A1* | 3/2011 | Chang | .................. | A61M 16/06 128/206.24 |
| 2012/0234326 A1* | 9/2012 | Mazzone | .............. | A61M 16/06 128/206.26 |
| 2013/0133659 A1* | 5/2013 | Ng | ........................ | A61M 16/06 128/205.25 |
| 2013/0133664 A1* | 5/2013 | Startare | ................ | A61M 16/06 128/206.24 |
| 2014/0166018 A1* | 6/2014 | Dravitzki | ............. | A61M 16/06 128/207.13 |
| 2014/0174446 A1* | 6/2014 | Prentice | ................ | A61M 16/06 128/205.25 |
| 2014/0261435 A1* | 9/2014 | Rothermel | ............ | A61M 16/06 128/205.25 |
| 2015/0047640 A1* | 2/2015 | McCaslin | ............. | A61M 16/06 128/205.25 |
| 2015/0328422 A1* | 11/2015 | Chodkowski | ......... | A61M 16/06 128/206.21 |

FOREIGN PATENT DOCUMENTS

| | | |
|---|---|---|
| WO | 2012020359 A1 | 2/2012 |
| WO | 2013068889 A1 | 5/2013 |
| WO | 2013144797 A1 | 10/2013 |

OTHER PUBLICATIONS

European Search Report from counterpart European Application EP20140898358, dated Aug. 22, 2016.
International Search Report, dated Jun. 2, 2015, in priority application PCT/CN2014/088757.

* cited by examiner

BREATHING MASK

CROSS REFERENCE OF RELATED APPLICATIONS

This application is Continuation Application of PCT application Serial No. PCT/CN2014/088757, filed on Oct. 16, 2014 which claims priority from CN Patent Application Serial No. 201410440090.6, filed on Sep. 1, 2014, the entire contents of which are incorporated herein by reference for all purposes.

FIELD OF THE INVENTION

The present invention relates to the field of assistant breathing apparatus, and particularly to a breathing mask for use in a respirator.

BACKGROUND OF THE INVENTION

A breathing mask for use in a respirator usually needs to be worn by a patient in a long period of time, and wearing comfort is one of standards for judging a level of performance of a breathing mask product. To ease a pressing feeling applied by a liner of the breathing mask to a facial portion of the patient, people usually fixedly arrange a forehead bracket connected with the liner. However, due to differences in race, age and height, different patients need forehead brackets of different sizes and angles.

The Chinese patent application CN101472637A discloses a forehead bracket of a mask, the forehead bracket comprises a frame connector, a forehead soft pad bracket and an adjusting knob, and an extension distance of the forehead soft pad bracket relative to the frame connector may be adjusted by turning the adjusting knob to make the forehead bracket fit for different patients. Although the forehead bracket of the mask can adapt for different patients while easing the pressing feeling applied by the liner to the facial portion of the patient, the adjusting knob needs to be manually adjusted. Thus, different patients have to adjust anew, and it is difficult to adjust the adjusting knob to an optimal comfort degree through manual adjustment, and therefore complicated adjustment is caused. In addition, the structure of the forehead bracket is relatively complicated, thus the requirements for the manufacturing process of the structure are high, and the production cost is also on the high side.

SUMMARY OF THE INVENTION

To solve the above problem, an object of the present invention is to provide a breathing mask for use in a respirator to achieve automatic adjustment of the forehead bracket without manual assistant adjustment.

The present invention provides a breathing mask for use in a respirator, comprising:

a receiving cover, comprising an engagement portion for engaging a patient's mouth portion and/or nose portion, a connection portion connected to a breathing pipe, and an elastic deformable portion for connecting the engagement portion with the connection portion; and, a forehead support, fixedly disposed external of the connection portion; wherein the forehead support is constructed swingable towards or away from the patient's forehead relative to the receiving cover when the elastic deformable portion is in a compressed state or a tensioned state.

The breathing mask according to the present invention, through movement of the forehead support and deformation of the elastic deformable portion, may achieve automatic adjustment of the forehead support without manual assistant adjustment.

In an embodiment, the elastic member can reduce a bent angle or a compressed distance of the flat structure during the forehead support is being adjusted, so that elasticity of the flat structure is enhanced and the service life of the flat structure is improved. In addition, by using the breathing mask according to the present invention, an action force from the head band of the breathing mask is shared by the forehead support so as to effectively reduce the action force applied by the head band to the receiving cover, thereby the pressing feeling applied by the receiving cover to the facial portion of the patient is effectively eased.

In addition, the breathing mask for use in the respirator according to the present invention is structurally simpler than a conventional breathing mask and thereby may substantially reduce the manufacturing process and cost. The breathing mask is used safely and stably and can be easily spread and applied.

BRIEF DESCRIPTION OF DRAWINGS

The present invention will be described below in more detail based on embodiments with reference to figures, wherein.

In the figures, the same parts are denoted by the same reference number. The figures are not drawn in an actual scale.

DETAILED DESCRIPTION OF PREFERRED EMBODIMENTS

The present invention will be further described in combination with figures.

Figure 1:
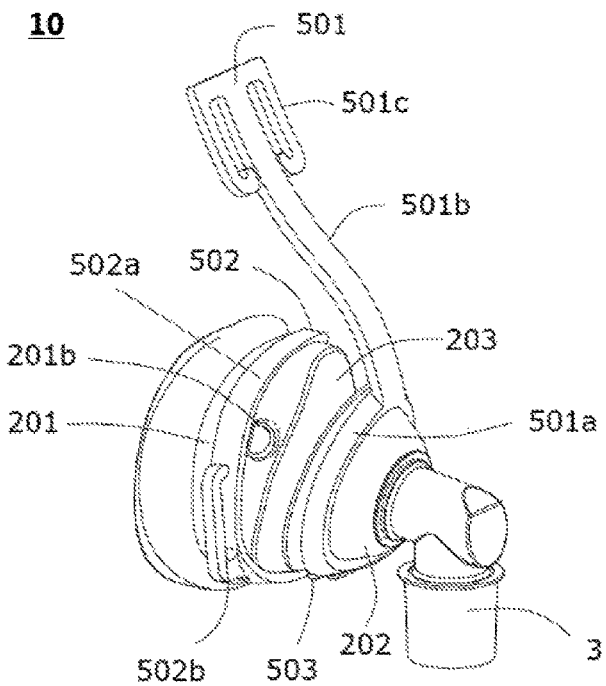
FIG. 1 illustrates a perspective view of a breathing mask for use in a respirator according to an embodiment of the present invention.
Figure 2:
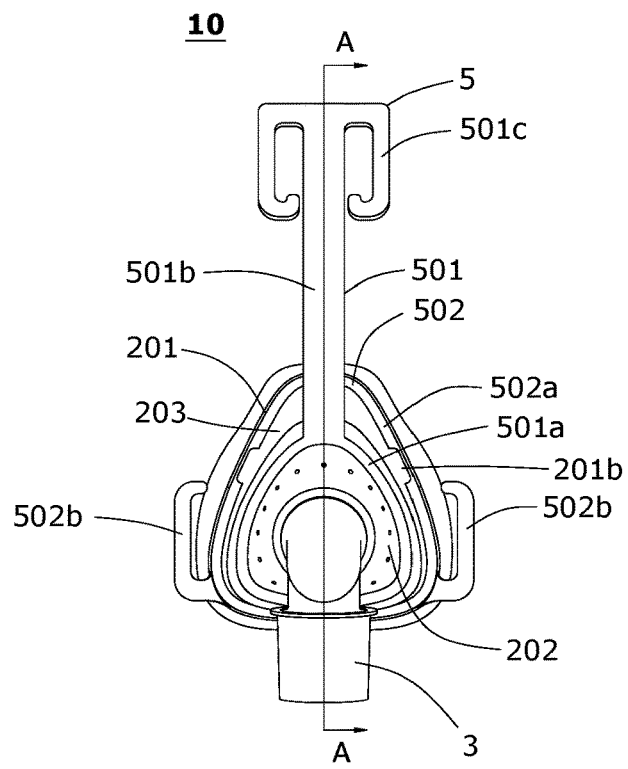
FIG. 2 illustrates a front view of a breathing mask for use in a respirator according to an embodiment of the present invention.

FIG. 1 and FIG. 2 both show a breathing mask 10 for use in a respirator according to an embodiment of the present invention, the respirator particularly may be a CPAP (Continuos Positive Airway Pressure) respirator, and the breathing mask 10 is used to deliver a CPAP air stream into a patient's respiratory tract.

Figure 3:
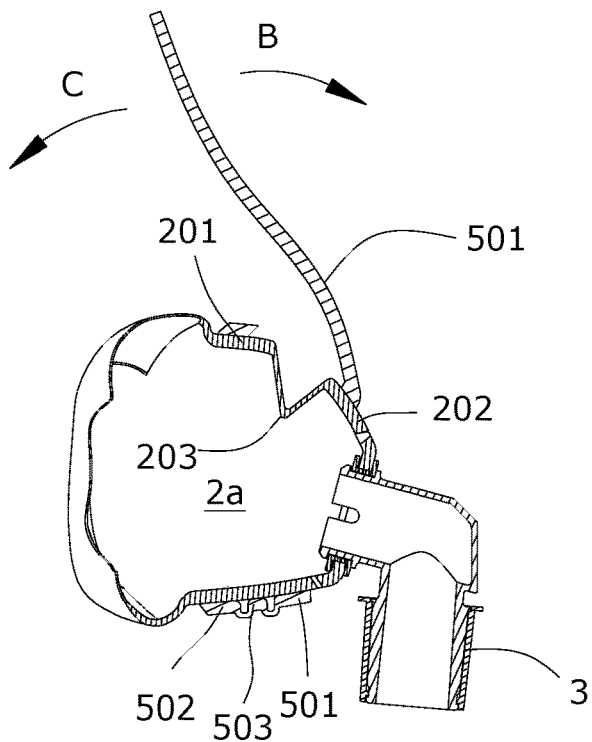
FIG. 3 illustrates a sectional view taken along line A-A of FIG. 2.

As shown in FIGS. 1 and 2, the breathing mask 10 comprises a receiving cover 2 having an inner cavity 2*a* (see FIG. 3). The receiving cover 2 comprises an engagement portion 201 for engaging the patient's mouth portion and/or nose portion, a connection portion 202 connected to a breathing pipe 3, and an elastic deformable portion 203 for connecting the engagement portion 201 with the connection portion 202. Wherein the breathing pipe 3 is preferably a curved or straight pipe and rotatably connected to the connection portion 202 of the receiving cover 2 so that the patient may adjust an orientation of the breathing pipe 3 connected to the receiving cover 2 to assist the patient in changing a posture, e.g., changing from lying on his back to lying on his side. The breathing pipe 3 is detachably connected to the connection portion 202 so that the breathing pipe 3 can be easily detached for washing. In other embodiments, the breathing pipe 3 may also be arranged undetachably connected to the connection portion 202.

Wrinkles in the elastic deformable portion 203 may be configured in a corrugated shape, a serrated pipe, a concave shape distributed in an arcuate shape along an outer surface of the receiving cover 2, or a convex shape distributed in an arcuate shape along the outer surface of the receiving cover 2. Certainly, those skilled in the art may configure the wrinkles in other shapes according to specific needs.

Figure 4:
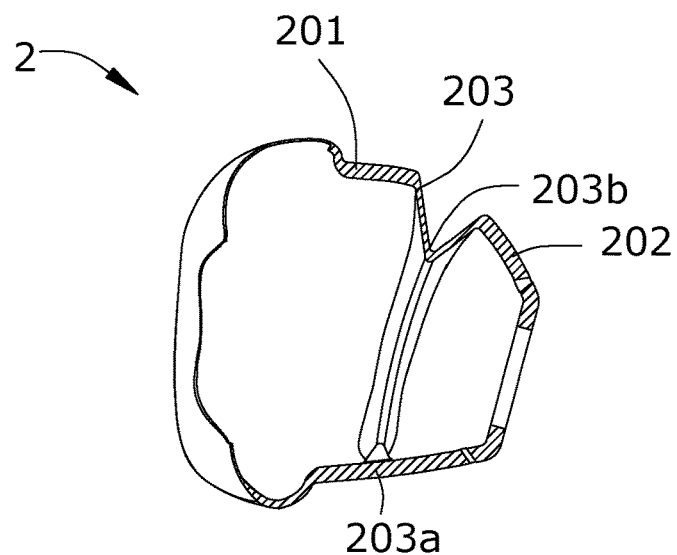
FIG. 4 illustrates a receiving cover of the breathing mask for use m a respirator according to an embodiment of the present invention.

In the present embodiment, the elastic deformable portion 203 comprises a flat portion 203a disposed on a bottom of the receiving cover 2 and a wrinkle structure 203b extending downward along both sides from a top of the receiving cover 2 to the flat structure 203a (see FIG. 4). The wrinkle structure 203b may be configured in the above mentioned concave shape or convex shape and has a U-shaped or V-shaped recess (a shape of a radial section) opening towards an exterior or interior of the receiving cover 2. Whilst ensuring a strength of the receiving cover 2, the flat structure 203a scatters an external force locally received by the receiving cover 2 to other portions; the wrinkle structure 203b is capable of deforming by expanding or contracting the opening to enable the engagement portion 201 of the receiving cover 2 stuck to the mouth portion or nose portion of the patient. In another embodiment, the elastic deformable portion 203 may only comprise a wrinkle structure extending downward along both sides from a top of the receiving cover 2 to the bottom. In this way, the wrinkle structure may deform by expanding or contracting the opening to enable the engagement portion 201 of the receiving cover 2 stuck to the mouth portion or nose portion of the patient.

In the present embodiment, the receiving cover 2 is directly constructed as a liner structure, and the liner structure may be made of rubber material, particularly of silicone material. In another embodiment, the engagement portion 201 of the receiving cover 2 may be directly constructed as a liner structure, and the liner structure is detachably connected to the elastic deformable portion 203. However, to meet the deformation needs, at least the elastic deformable portion 203 in the receiving cover 2 needs to be constructed as an elastic portion, and it may be made of an elastic material, e.g., of rubber.

The breathing mask 10 for use in the respirator according to the present invention comprises a bracket assembly 5. As shown in FIG. 1, the bracket assembly 5 comprises a forehead support 501 disposed external of the connection portion 202 and a receiving cover fixing frame 502 fixedly disposed external of the engagement portion 201, and an elastic member 503 disposed at the bottom of the receiving cover 2 and used for connecting the forehead support 501 with the receiving cover fixing frame 502. The elastic member 503 may be constructed as a sheet having an M-shaped longitudinal cross section (namely, the cross section as shown by FIG. 3), and it can get stuck to the flat structure 203a of the elastic deformable portion 203. Both the forehead support 501 and receiving cover fixing frame 502 may be made of resin material, whereas the elastic member 503 may be made of resin or rubber material.

When the patient fits the receiving cover 2 to his mouth portion and/or nose portion, the forehead support 501 contacts the patient's forehead. As different patient's foreheads protrude at different heights, a predetermined angle between the forehead support 501 and the receiving cover 2 may not be certainly fit for all patients. Therefore, when the forehead support 501 abuts against the forehead, the forehead support 501 needs to be swung relative to the receiving cover 2 in a first direction B (away from the patient's forehead) or a second direction C (towards the patient's forehead) opposite to the first direction B so as to adapt for different patients. Specifically, when a desired angle between the forehead support 501 and receiving cover 2 is larger than the predetermined angle (namely, when the patient's forehead is more protruding), the forehead will urges the forehead support 501 to be swung in the first direction B so that the wrinkle structure 203b of the receiving cover 2 expands a recessed opening under action of the forehead support 501 (namely, a tensioned state); when a desired angle between the forehead support 501 and receiving cover 2 is smaller than the predetermined angle (namely, when the patient's forehead is lower), the forehead will urges the forehead support 501 to be swung in the second direction C so that the wrinkle structure 203b of the receiving cover 2 reduces the recessed opening under action of the forehead support 501 (namely, a compressed state). As known from the above, the breathing mask 10 of the present invention may achieve automatic adjustment of the forehead support 501 without manual assistant adjustment. At the same time, as the elastic member 503 can enhance elasticity of the flat structure 203a, it can reduce a bent angle or a compressed distance of the flat structure 203a during the forehead support 501 is being swung, the service life of the flat structure 203a is consequently improved.

Figure 5:
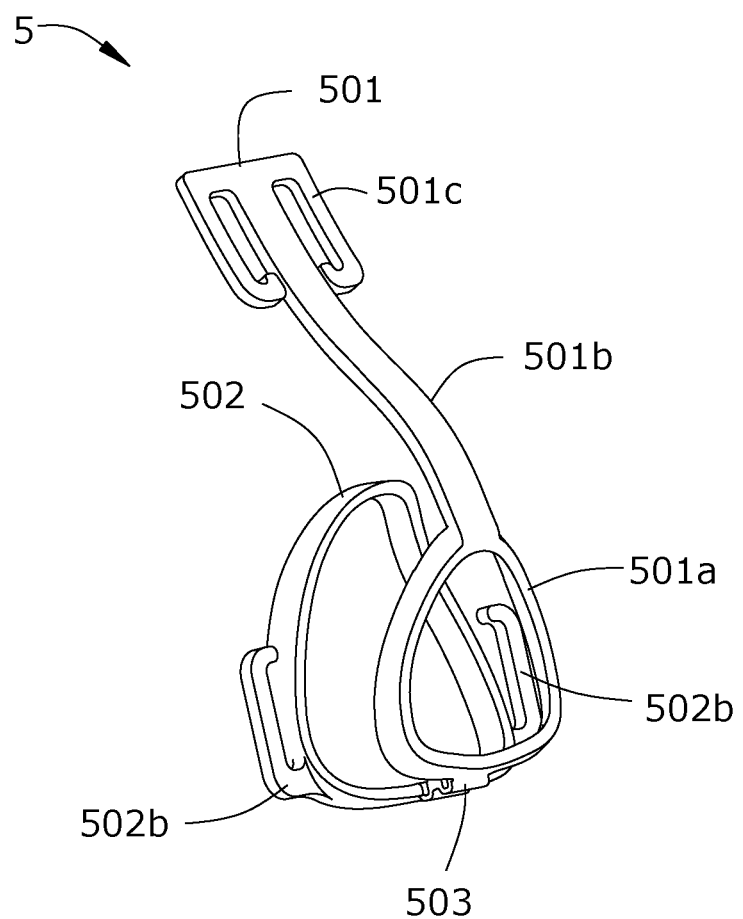
FIG. 5 illustrates a bracket assembly of the breathing mask for use in a respirator according to an embodiment of the present invention.

In the embodiment shown in FIG. 5, the forehead support 501 comprises an annular portion 501a sleeved around the connection portion 202, a bar-shaped curved rack 501b fixed on the annular portion 501a and adapted to be stuck on the patient forehead, and a first connection structure 501c disposed at a top end of the rack 501b and used to mount a head band. The receiving cover fixing frame 502 comprises a matching sleeve 502a fixed around the engagement portion 201 and a second connection structure 502b disposed on the matching sleeve 502a and used to mount the head band. Both the first connection structure 501c and second connection structure 502b are preferably a double-hook structure for quick and detachable installation of the head band of the breathing mask 10. Wherein the head band is well known by those skilled in the art and will not be detailed herein.

In an embodiment, since the automatic adjustment of the forehead support 501 is mainly achieved by the deformation of the elastic deformable portion 203, the elastic member 503 may not be included in the breathing mask 10, and the receiving cover fixing frame 502 which is connected to the elastic deformable portion 203 also may not be included in the breathing mask 10. The head band may be directly mounted on the first connection structure 501c and the receiving cover 2 in this case.

In an embodiment, the engagement portion 201 comprises two positioning shoulders respectively disposed on two sides of the matching sleeve 502a, and a plurality of positioning protrusions 201b also disposed on the two sides of the matching sleeve 502a. In this way, while the matching sleeve 502a is stably fixed, it may be easily detached from the positioning protrusions 201b of the engagement portion 201. In the engagement portion 201, the top surface of the positioning shoulder is higher than a matching portion for mounting the matching sleeve 502a, and the plurality of positioning protrusions 201b are preferably two protrusions arranged radially opposite to each other. The positioning protrusions 201b are arranged at a middle position between the top and bottom of the engagement portion 201 so as to allow for more steady and stable positioning.

It should be understood that, according to practical requirements, the positions and quantity of the positioning shoulders and the positioning protrusions 201b may be modified. In an embodiment of the present invention, only one positioning shoulder may be included and disposed on one side of the matching sleeve 502a, and the plurality of positioning protrusions 201b may be disposed on the other side of the matching sleeve 502a. Thus, the positions and quantity of the positioning shoulders and the positioning protrusions 201b cannot be used to limit the protection scope of the present invention.

To conclude, the breathing mask 10 for use in the respirator according to the present invention may achieve automatic adjustment of the forehead support 501 without manual assistant adjustment. Meanwhile, by using the breathing mask 10 for use in the respirator according to the present invention, an action force from the head band of the breathing mask is shared by the forehead support 501 so as to reduce the action force applied by the head band to the receiving cover 2, thereby the pressing feeling applied by the receiving cover 2 to the facial portion of the patient is effectively eased. In addition, the breathing mask 10 for use in the respirator according to the present invention is structurally simpler than a conventional breathing mask and thereby the manufacturing process and cost are reduced.

Although the present invention is already described with reference to preferred embodiments, various improvements may be made thereto and equivalents may be used to replace parts therein without departing from the scope of the present invention. Particularly, so long as there are not structural conflicts, technical features mentioned in the embodiments may be combined in any manner. The present invention is not limited to specific embodiments disclosed in the text herein, but includes all technical solutions falling within the scope of the appended claims.

What is claimed is:

1. A breathing mask, comprising:
   a receiving cover, comprising an engagement portion for engaging a patient's mouth portion and/or nose portion, a connection portion connected to a breathing pipe, and an elastic deformable portion for connecting the engagement portion with the connection portion;
   a forehead support, fixedly disposed on the connection portion; wherein the forehead support is constructed swingable towards or away from the patient's forehead relative to the receiving cover when the elastic deformable portion is in a compressed state or a tensioned state, respectively;
   a receiving cover fixing frame, fixedly disposed external of the engagement portion; and,
   an elastic member, disposed at a bottom of the receiving cover and used for connecting the forehead support with the receiving cover fixing frame.

2. The breathing mask according to claim 1, wherein the elastic deformable portion comprises:
   a flat structure, disposed on a bottom of the receiving cover; and
   a wrinkle structure, extending downward along both sides from a top of the receiving cover to the flat structure.

3. The breathing mask according to claim 2, wherein the wrinkle structure is constructed as a corrugated shape, a serrated pipe, a concave shape, or a convex shape.

4. The breathing mask according to claim 2, wherein the wrinkle structure has a U-shaped or V-shaped recess opening towards an exterior or interior of the receiving cover.

5. The breathing mask according to claim 1, wherein the elastic deformable portion is a wrinkle structure extending downward along both sides from a top of the receiving cover to a bottom of the receiving cover.

6. The breathing mask according to claim 1, the elastic deformable portion is made of rubber material.

7. The breathing mask according to claim 1, wherein the forehead support comprises:
   an annular portion, sleeved around the connection portion;
   a rack, disposed on the annular portion and adapted to be stuck on the patient's forehead; and,
   a first connection structure, disposed at a top end of the rack and used to mount a head band.

8. The breathing mask according to claim 7, wherein the first connection structure is constructed as a double-hook structure.

9. The breathing mask according to claim 7, wherein the rack is bar-shaped and curved.

10. The breathing mask according to claim 1, wherein the elastic member is constructed as a sheet having an M-shaped cross section.

11. The breathing mask according to claim 1, wherein the receiving cover fixing frame comprises:
    a matching sleeve, fixed around the engagement portion; and,
    a second connection structure, disposed on the matching sleeve and used to mount a head band.

12. The breathing mask according to claim 11, wherein the second connection structure is constructed as a double-hook structure.

13. The breathing mask according to claim 11, wherein the engagement portion comprises:
    two positioning shoulders respectively disposed on two sides of the matching sleeve; and/or,
    a plurality of positioning protrusions disposed on the two sides of the matching sleeve.

14. The breathing mask according to claim 13, wherein the plurality of positioning protrusions comprises two protrusions arranged radially opposite to each other.

15. The breathing mask according to claim 13, wherein the plurality of positioning protrusions is disposed at a middle position between a top and a bottom of the engagement portion.

16. The breathing mask according to claim 1, wherein the forehead support and the receiving cover fixing frame are made of resin material; and/or,
    the elastic member is made of resin or rubber material.

17. The breathing mask according to claim 1, wherein the receiving cover is constructed as a liner structure.

18. The breathing mask according to claim 1, wherein the engagement portion of the receiving cover is constructed as a liner structure, and the liner structure is detachably connected to the elastic deformable portion.

19. The breathing mask according to claim 1, wherein the connection portion of the receiving cover is constructed to be rotatably connected to the breathing pipe.

* * * * *